US012784893B2

(12) United States Patent
Burnett et al.

(10) Patent No.: US 12,784,893 B2
(45) Date of Patent: Nov. 3, 2026

(54) EFFICIENT CACHING FOR RADIOTHERAPY OBJECT VISUALIZATION AND PROCESSING

(71) Applicant: Elekta, Inc., Atlanta, GA (US)

(72) Inventors: Kyle Thomas Burnett, Orlando, FL (US); Salvadore Anthony Gerace, Orlando, FL (US); Todd Joseph Wilfling, St. Louis, MO (US)

(73) Assignee: Elekta, Inc., Atlanta, GA (US)

( * ) Notice: Subject to any disclaimer, the term of this patent is extended or adjusted under 35 U.S.C. 154(b) by 392 days.

(21) Appl. No.: 18/494,475

(22) Filed: Oct. 25, 2023

(65) Prior Publication Data

US 2025/0140379 A1 May 1, 2025

(51) Int. Cl.
*G16H 30/20* (2018.01)
*H04L 9/08* (2006.01)

(52) U.S. Cl.
CPC ........... *G16H 30/20* (2018.01); *H04L 9/0819* (2013.01)

(58) Field of Classification Search
None
See application file for complete search history.

(56) References Cited

U.S. PATENT DOCUMENTS

2020/0007531 A1* 1/2020 Koottayi ............... H04L 67/146
2023/0057802 A1* 2/2023 Yoches ............... G06F 16/9574
2024/0123258 A1* 4/2024 Wang ................... A61N 5/1064

FOREIGN PATENT DOCUMENTS

WO 2021090063 5/2021

OTHER PUBLICATIONS

"European Application Serial No. 24208793.0, Extended European Search Report mailed Mar. 17, 2025", 13 pgs.
"European Application Serial No. 24208793.0, Response filed Oct. 13, 2025 to Extended European Search Report mailed Mar. 17, 2025", 29 pgs.

* cited by examiner

*Primary Examiner* — Helen Zong
(74) *Attorney, Agent, or Firm* — Schwegman Lundberg & Woessner, P.A.

(57) ABSTRACT

Systems and techniques may be used for visualization of radiation therapy data. An example method may include determining a data set corresponding to visualization data to be displayed in an application user interface (e.g., on a client device). The data set may include one or more Digital Imaging and Communications in Medicine (DICOM) objects. A request for the data set may be received at an application programming interface (API) configured to access multiple sources of DICOM objects. The method may include processing the requested data set, verifying the request for the data set, and upon the verifying, providing the client device with access to the processed data set to enable visualization of the processed data set. The processed data set may be cached, and verified requests for the same data set may be provided access to the cached processed data to visualize at the same or different client device.

21 Claims, 6 Drawing Sheets

EFFICIENT CACHING FOR RADIOTHERAPY OBJECT VISUALIZATION AND PROCESSING

BACKGROUND

Radiation therapy (RT) or "radiotherapy" may be used to treat cancers or other ailments in mammalian (e.g., human and animal) tissue. The processing of RT or medical imaging data objects is commonly performed by a software application. Users of different RT software applications may be interested in visualizing the same underlying data. An RT visualizer may manage or handle patient health information (PHI), which may be provided from a Digital Imaging Communication in Medicine (DICOM) file as a DICOM object, for example, as the visualizer renders data from the DICOM file.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
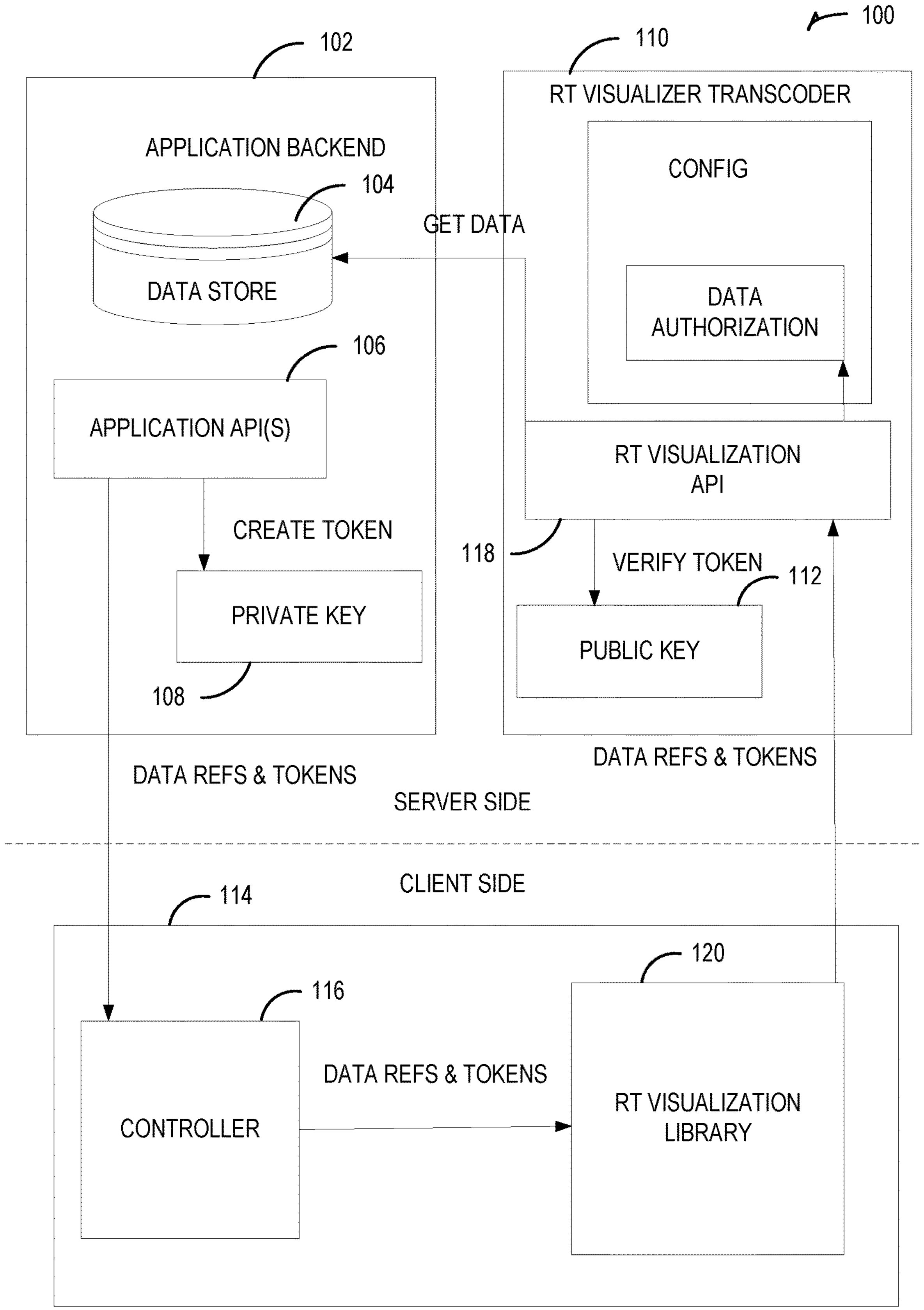
FIG. 1 illustrates an example of an end-to-end data flow for authorization of a radiation therapy data visualization request.

In the following detailed description, reference is made to the accompanying drawings which form a part hereof, and which is shown by way of illustration-specific embodiments in which the techniques presently disclosed may be practiced. These embodiments, which are also referred to herein as "examples," are described in sufficient detail to enable those skilled in the art to practice the invention, and it is to be understood that the embodiments may be combined, or that other embodiments may be utilized and that structural, logical, or other changes may be made without departing from the scope of the present disclosure. The following detailed description is, therefore, not be taken in a limiting sense, and the scope of the present disclosure is defined by the appended claims and their equivalents.

Systems and techniques described herein may be used for radiation therapy visualization. For example, a data set corresponding to visualization data to be displayed in an application user interface on a programming device may be determined. The data set may include one or more medical imaging objects such as one or more Digital Imaging and Communications in Medicine (DICOM) data objects (referred to herein as a "DICOM object"). A DICOM object may include a special attribute containing image pixel data. A modality attribute generally describes the types of image data that is captured from a patient (e.g., a Computed Tomography (CT) scan, or the like). A DICOM object may be a real-world information entity that includes information such as patient data, an imaging study, a medical device, a physician's visit, a document, a diagnostic interpretation or the like. A DICOM object may include a number of attributes including items such as a name or other identification information of a patient.

A request for the data set may be received at an application programming interface (API) configured to access multiple sources of DICOM objects and/or to operate in an environment comprising multiple sources of DICOM objects (e.g., multiple databases containing DICOM objects). The environment may comprise multiple sources of DICOM objects and include a multi-application and/or a multi-tenant environment (e.g., at the client side and/or the server side). The requested data set may be processed, which may include optimizing the requested data set. Optimizing the requested data set may include optimizing the requested data set for visualization (at the client device) without visualizing or visually rendering the data set at the device or server processing the requested data. For example, pixel data may be extracted from one or more DICOM objects in the requested data set to remove personal health information or other identifying information prior to providing the client device access to the processed data. Thus, data may be extracted from the DICOM tags and placed in a JSON object which may be parsed in web-based client applications. Optimizing the requested data set for visualization without visualizing or rendering the requested data set has the effect of making the data set better suited for downstreaming (e.g., use on different client devices) and for caching the requested data both at the server level and the client level. The anonymized and optimized (the processed) data may be rendered by the client device without using additional server level resources.

A secure key may be created corresponding to the one or more DICOM objects. The request for the data set at the API may include the secure key, which may be unique to the API request and only allow access to a specific combination of the one or more DICOM objects in the data set. When the API request is received (e.g., at a server) the secure key may be verified, to confirm that the secure key corresponds to the requested data set. In an example, the secure key may be provided in a JSON web token (JWT). To verify that the secure key corresponds to the requested data set, the API may validate the JWT using a public key. The public key may be configured to validate that the client device is a valid source to request the data set and validate that the request for the data set has not been modified or corrupted while in transit from the client device.

RT visualizers may rely on caching mechanisms to ensure optimal performance and to minimize duplication of processed data and to reduce or minimize processing time. Thus, the optimized data set may be cached (e.g., at the server side or level) and the API may retrieve the requested data set from a cached data source. A second request for the data set may be sent to the API such as from a second client device. The second request may include a second secure key. In response to a verification that the second secure key corresponds to the requested data set, the second client device may be provided access to the cached optimized data set for visualization or rendering (without the need to process the data set a second time).

In other RT visualization systems, processed result data might be reused across user sessions within an application, but cannot be reused across different applications or devices since processed data is often in a proprietary format only known to the application that performed the processing. Thus, if the same data needs to be accessed by multiple applications or client side devices, the same data needs to be processed for each application or user session. Reprocessing the data multiple times can lead to increase costs both in terms of data storage and processing. The presently claimed systems and methods introduce caching mechanisms to optimize the data and reduce, lower, or minimize the duplication of processed data and processing time. With the presently disclosed systems and methods, data to be visualized will only need to be processed one time (unless the cache is evicted) and may be accessed across multiple sessions and/or multiple devices upon verification that the device is authorized to visualize the processed data.

An RT visualizer transcoder may work in multi-tenant and multi-application environments. The RT visualizer may have unrestricted access to the underlying data sources, the underlying data sources containing data from different applications and tenants. It is important that client-side actors be allowed to only view data that they have been authorized to view. A canonical digest of each request to visualize one or more of the DICOM objects may be computed and the digest payload may be signed with a private key to produce the JSON Web Token. The digest may encode an identifier of the data source (e.g., the network drive or cloud storage location where the data can be found) and the unique and immutable data identifiers within that source. The RT Visualizer transcoder server may verify the token using a public key, decode the token to extract the digest, and compute its own digest to compare against the one encoded into the token. This process verifies what data the token corresponds to and confirms that the request is valid for the data being sought by the client side device (e.g., that the client side device is authorized to access the data).

Upon successful verification, the transcoder server may check to see whether the requested data has already been processed and stored in the cache. If the requested data is not available in the cache, the requested data may be fetched, processed, and stored in the cache. Once the data is stored in the cache, the stored data may be provided to any device or application pursuant to the verification process. Data in the cache may be safely evicted at any time. When the data in the cache has been evicted, requests for the evicted data will require the data to be fetched, processed, and stored in the cache again.

The present systems and methods thus represent an improvement over previous RT visualization techniques that utilize the cloud to process data for reuse across different user sessions (by the same application) but do not process data to be used across multiple applications. The presently disclosed systems and methods support the reuse of the processed data which obviates the need to use compute resources to recompute the data for each application. In addition, storage space is conserved because the processed data may only need to be stored once (as opposed to once per application). This may lead to lower latency for an end user when the system has already cached the data being requested. The visualization may also be consistent from application to application since the processed data being used by each application is identical. This has the additional advantage of standardizing a visualization pipeline between the application and the server while keeping unrelated application-specific aspects separate.

FIG. 1 illustrates an example of an end-to-end data flow (data flow 100) for authorization of a radiation therapy data visualization request. As a part of the data flow 100, an application backend 102 may include a data store 104 and one or more application programing interfaces (server-side API 106). The application backend 102 may determine data that a client will display and create a secure key or a private key 108. The private key 108 may be unique to the server-side API 106 request and only allow access to a specific combination of one or more DICOM objects in the data store 104. The private key 108 may be provided in a JSON Web Token (JWT). Hence, authorization may be independently configured for each data source (e.g., each DICOM object) in the data store 104. The configuration may be implemented by specifying a security field in a configuration section related to the particular source. The configuration may indicate a path to a public key (discussed below) used to validate any JWTs that are provided to the client (and subsequently sent to an RT visualizer transcoder (a transcoder server 110) discussed below). The JWT may be valid only for a certain data object and may not be used to reference any other data.

The purpose of the JWT includes allowing the transcoder server 110 to determine whether or not the bearer of the JWT should be granted access to the requested data. In an example, the JWT may contain a list of all related data objects that are requested, however, for many DICOM data types, such as image sets, the list of related data items may be quite large (e.g., several hundred or more items). In turn, the JWT associated with the request may become extremely large. To avoid creating large tokens, the JWT sent to the transcoder server 110 may contain a specific message digest with a hash of all of the requested data. The digest may be calculated the same way on both the application backend 102 server (which may determine whether the current user should have access to the requested data) and the transcoder server 110, which allows the transcoder server 110 to ensure that any data requested is authorized.

The process of generating a valid JWT may include the following operations:

- Perform a JSON.stringify( ) method on an entire data field from the client-side object. The data field may contain a list of images, structure set, plan, dose, or the like, to be visualized;
- Generate a hash of the stringified data using the same hashing algorithm that will be used to hash the JWT (e.g., an RS256 signing algorithm);
- Once the hash digest is generated, create a hexadecimal encoded string of the hash digest;
- Create a JWT payload with the data equal to the digest string; and
- Generate the JWT using the private key 108 that corresponds to a public key 112, that is configured for the target source.

In an example, all requests targeting any source that is been configured with an authorization will require a valid JWT. The JWT may be provided as a bearer token. When utilizing the client-side RT visualizer library 120, the token may be provided via the corresponding "add" method from the model.

The transcoder server 110 (the server-side RT visualizer) may rely heavily on caching mechanisms to provide optimal performance. The data may only need to be processed once, (unless the cache is evicted) and then the processed data may be provided to multiple applications or during multiple sessions. Since the transcoder server 110 does not need to retrieve the cached data from the underlying data source, enforcement of access control rules are necessary when fetching data from the cache. Hence, all data for an object must be tied to that object via the digest, which is inherent and unique to the object. An example end-to-end data flow may include:

- The application backend 102 may determine the data that the client may display such as on a client-side application user interface 114, and create a corresponding bearer token including the private key 108;
- Data references and the token may be passed or transmitted from the server-side API 106 to a renderer (controller 116) of the client-side application user interface 114. The controller 116 may, in turn, pass the data references and token to the client-side RT visualizer library 120;
- The data references and tokens may be passed or transmitted from the client-side RT visualizer library 120 to a server-side RT visualization API 118 on or coupled to the transcoder server 110;
- The transcoder server 110 may use the public key 112 to validate the authenticity of the JWT by ensuring that the request is from a correct tenant or client source (e.g., ensuring that the public-private key pairs are unique), that the data claim has not been corrupted or modified in transit from the client-side RT visualizer library 120 to the server-side RT visualization API 118, and that the JWT is valid for or corresponds to the data being requested;
- Upon verification of the request and verification of the JWT, the transcoder server 110 may connect to data store 104 using the verified credentials and access the requested data. From there, the requested data may be cached (as discussed below) to be visualized for subsequent requests.

Figure 2A:
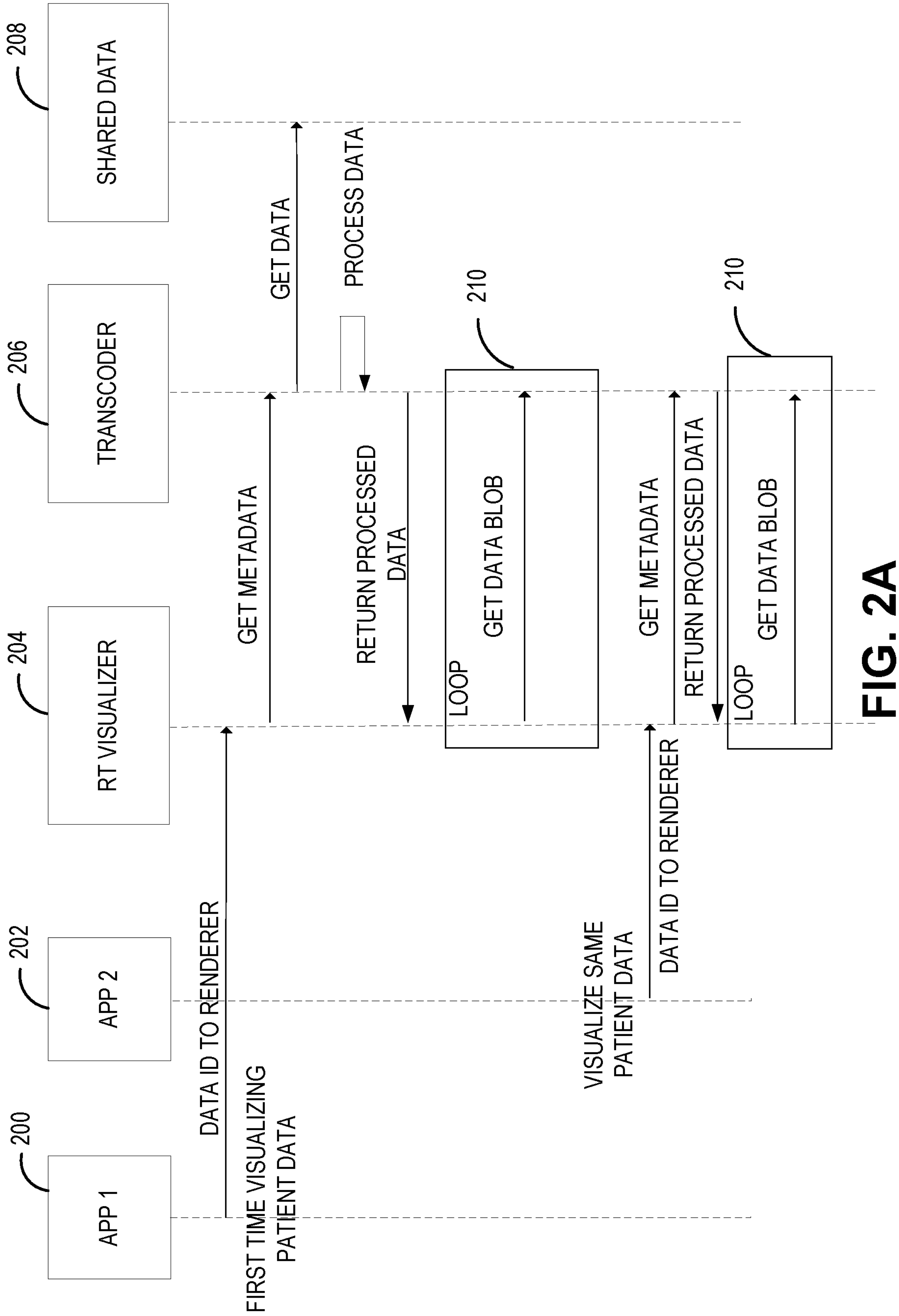
FIGS. 2A and 2B illustrate a visualization sequence for radiotherapy visualization.
Figure 2B:
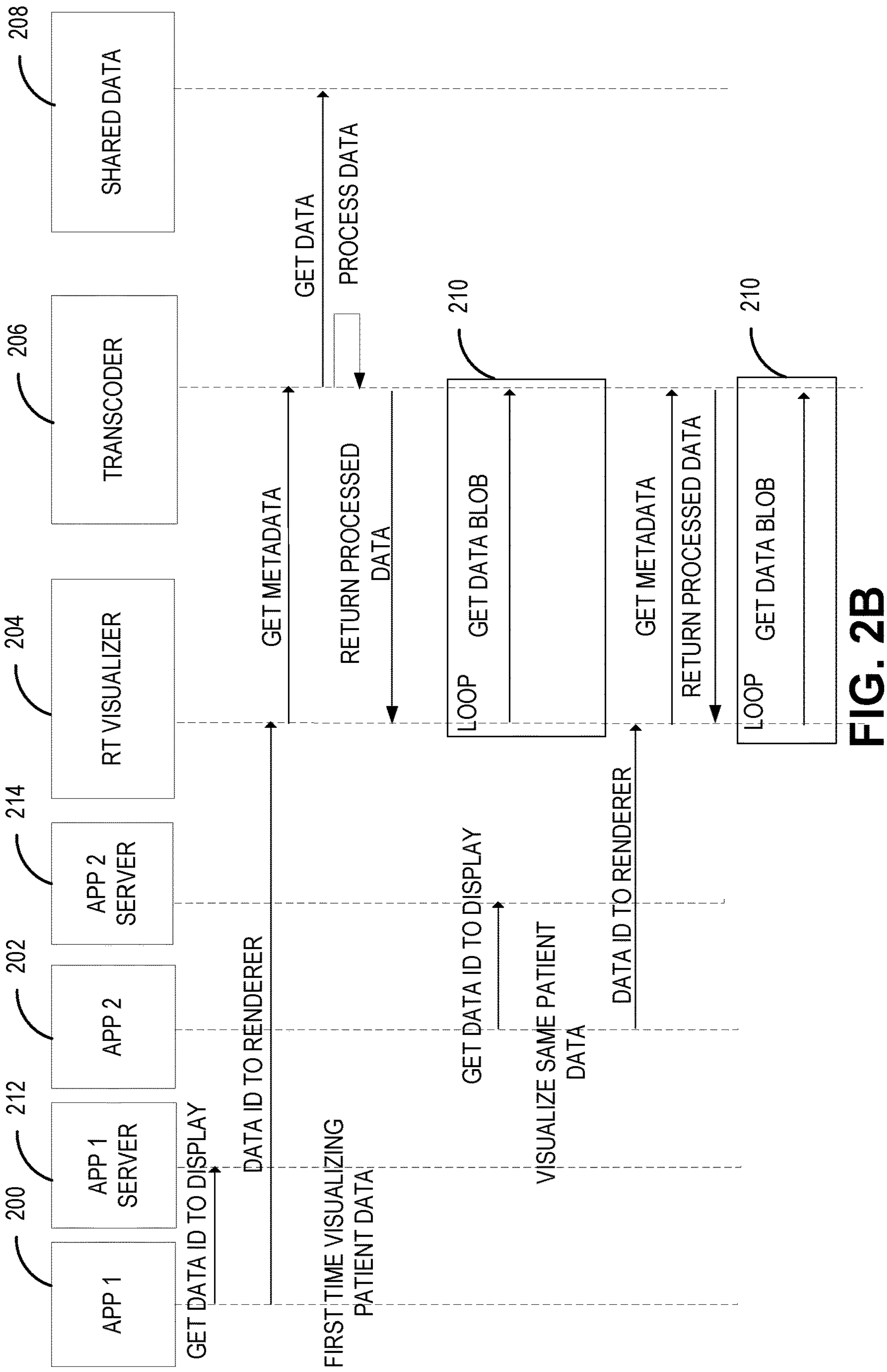

FIGS. 2A and 2B illustrate a visualization sequence for radiotherapy visualization. As illustrated in FIG. 2A, a first client application 200 may transmit a data request including data identification information to an RT visualizer 204, a renderer, or the like. The RT visualizer 204 may be implemented on a server, such as illustrated in FIG. 1. The RT visualizer 204 may transmit a request to a transcoder 206 for metadata. The metadata may include one or more DICOM objects or other medical imaging data or patient data. The first time visualizing the patient data, the transcoder 206 may transmit a request to a shared data source 208.

After the transcoder 206 fetches the data from the shared data source 208, the transcoder 206 may process the data and return the processed metadata to the RT visualizer 204 for visualization by the first client application 200. The processed data blob may be stored in cache 210, so that when a request from a second client application 202, for the same data requested by the first client application 200 may be fetched from the cache 210. The data blob may include several pieces of data to be fetched in order to render what is requested. That is, a request to visualize the same patient data may be sent from the second client application 202 to the RT visualizer 204. The RT visualizer 204 may again attempt to fetch the metadata from the transcoder 206, but since the data has already been processed and cached, the processed metadata (the data blob) may be returned immediately from the cache 210 to the RT visualizer 204 for visualization by the second client application 202. Therefore, the request from the second client application 202 for the same data that was requested by the first client application 200 may not need to be fetched from the shared data source 208 by the transcoder 206 and processed a second time. Thus, any subsequent requests for the processed data may be sent from the cache 210 to be downloaded and visualized by client-side devices, saving computing resources of the server so long as the cache 210 has not been cleared.

As illustrated in the example of FIG. 2B, the first client application 200 may retrieve the data identification information from a first application server 212, and then send the request to the RT visualizer 204. Similarly, the second client application 202 may retrieve data identification information from a second application server 214, and then send the request for the data to the RT visualizer 204. Once the applications receive the data identification information from the respective servers, the process may proceed as described for FIG. 2A.

Figure 3:
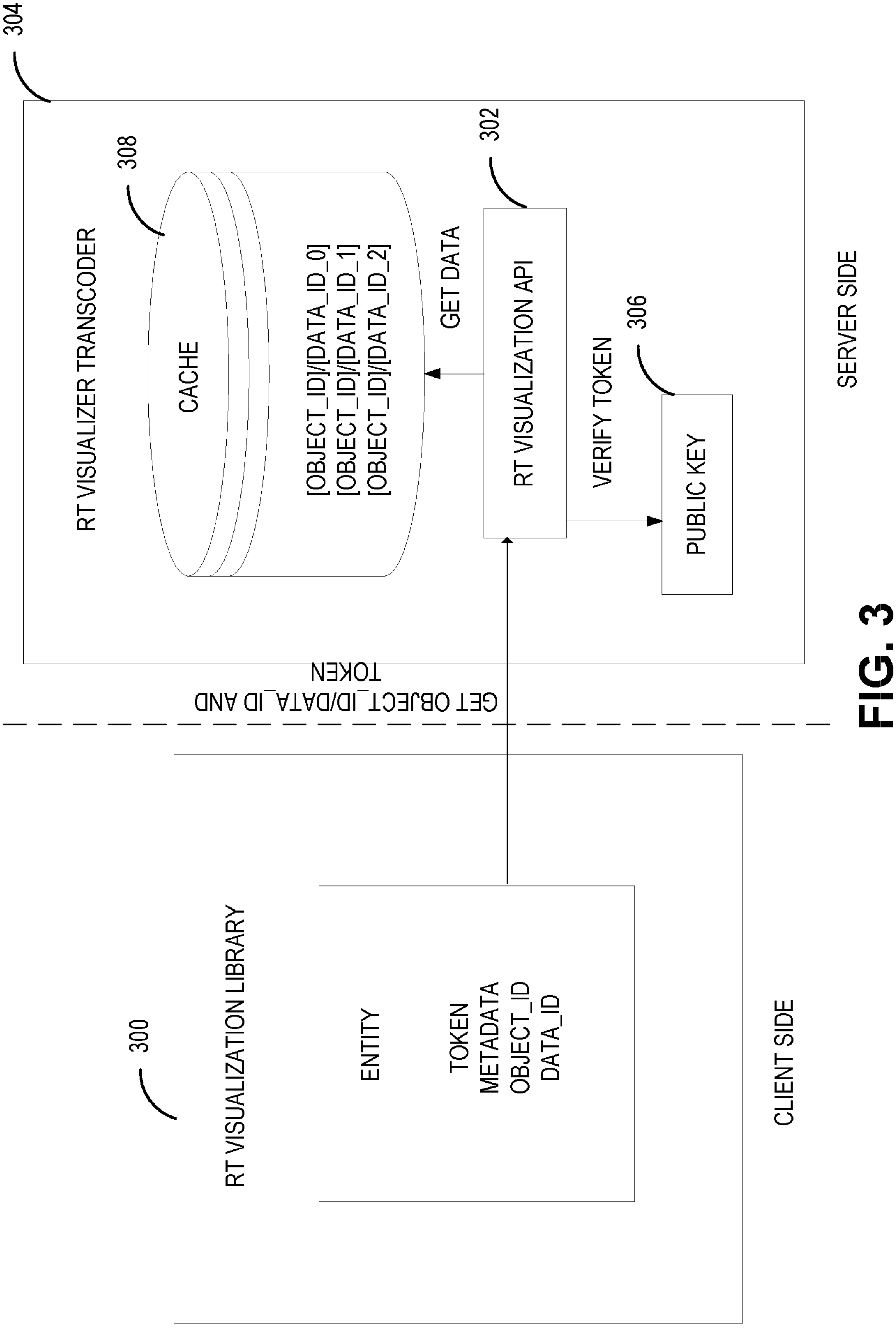
FIG. 3 illustrates an example data flow for retrieving cached data.

FIG. 3 illustrates an example data flow for retrieving cached data. In the example illustrated in FIG. 3, an RT visualizer 300 (such as those discussed above for FIGS. 1-2B) may transmit a GET request, containing an object identification, a data identification and the JWT, to a server-side RT visualization API 302 of or coupled to an RT visualizer transcoder 304. The RT visualizer transcoder 304 may use a public key 306 to decode the JWT. In such an example, the JWT is the same token discussed above for FIG. 1 and includes the private key 108. Decoding the JWT may include ensuring that the request is from a correct client or tenant source (e.g., that the private/public key pairs are unique) and ensuring that the data claim (the GET request) has not been modified, altered, or otherwise corrupted in transit from the client side. Once the JWT is decoded and the information verified, the RT visualizer transcoder 304 may access the requested processed data from cache 308.

Figure 4:
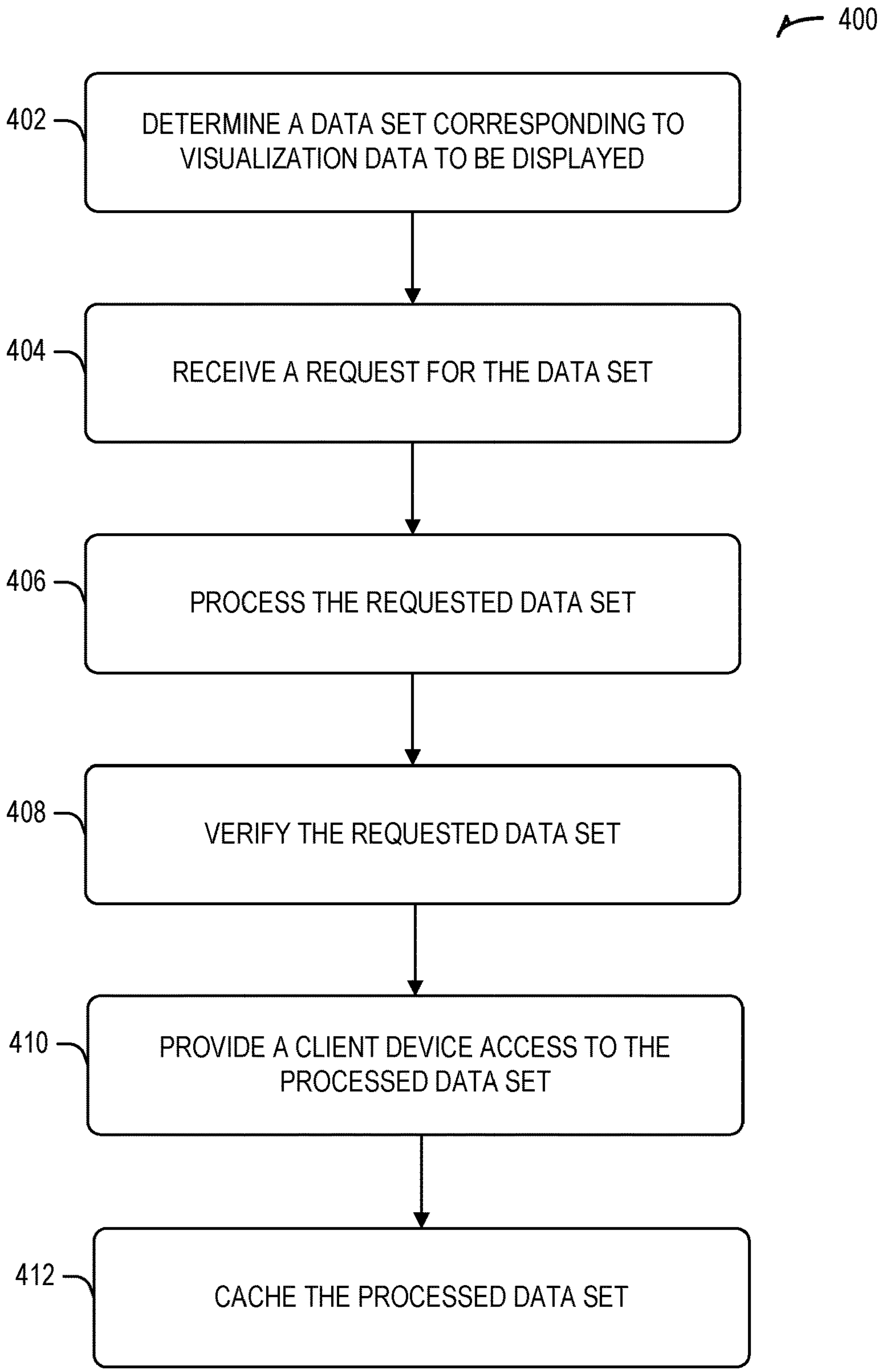
FIG. 4 illustrates an example method of radiation therapy visualization.

FIG. 4 illustrates an example method of radiation therapy visualization. The method 400 may include or comprise a number of Operations (402-412). These Operations are examples only, and the executed method may omit one or more of the listed Operations, may repeat Operations, may include other Operations, or may execute the Operations concurrently, substantially simultaneously, or in another order, as appropriate or desired. The Operations may be performed automatically by a processor or controller of a machine or computer, such as described below for FIG. 5.

At Operation 402, the method 400 may include determining a data set corresponding to visualization data to be displayed in an application user interface on a client device. The data set may include one or more medical imaging objects, such as one or more DICOM objects, patient data, or other patient information. At Operation 404, the method 400 may include receiving a request for the data set at an application programming interface (API). The API may be configured to access multiple sources of DICOM objects, such as multiple databases or data stores. The environment may include a multi-tenant application and a multi-tenant environment. A secure key may be generated that corresponds to the DICOM objects. The secure key may be unique to the API request and may only allow access to a specific combination of the one or more DICOM objects in the data set.

The secure key may be provided in a JSON web token (JWT). The secure key may include a message digest. The message digest may include a hash generated from a list of the DICOM objects. For example, the hash may be generated from a list of images (e.g., radiotherapy images, computed tomography (CT) images, magnetic resonance (MR) images, or the like), one or more spatial registration objects, a structure set, a radiotherapy plan, and/or a radiotherapy dose to be visualized.

At Operation 406, the method 400 may include processing the requested data set. Processing the requested data set may include removing identifying information of a patient. Removing the identifying information may include removing or extracting pixel data from the one or more DICOM objects. For example, when personal and/or identifying information is burned on an image such as a CT scan, the pixels with the identifying information may be extracted during the processing. Further, processing the requested data set may include optimizing the requested data set for visualization without visualizing or visually rendering the requested data set at the API. Such processing of the requested data set may allow the data set to efficiently be used on different client devices and for caching the requested data set both at the client level and the server level.

At Operation 408, the method 400 may include verifying the requested data set, and Operation 410 may include providing a client device access to the processed data set. For example, the requested data set may be verified by verifying that the secure key corresponds to the requested data set. As a part of this verification, the API may validate the JWT using a public key. The public key may validate that the client device is a valid source to request the data set and validate that the request for the data set has not been modified or corrupted in transit from the client device. Thus, the API may validate the private-public key pair and verify that the secure keys correspond to the requested data. Once the requested data and the secure keys are verified, the client device may be allowed to render the processed data set in an application user interface of or on the client device.

At Operation 412, the method 400 may include caching the processed data set. The cached data set may be stored in memory of a server, or a database coupled to the server. Once the data set is cached, a request to visualize the same processed data (e.g., a second request), when submitted and verified through the process discussed above, the client device or a second client device may be provided accessed to the cached data set. It is understood that Operations 410 and 412 may be performed in either order. For example, the client device may be provided access to the processed data before the processed data is cached. Alternatively, the processed data may be cached, and then the client device may be provided access to the processed data from the cache.

Figure 5:
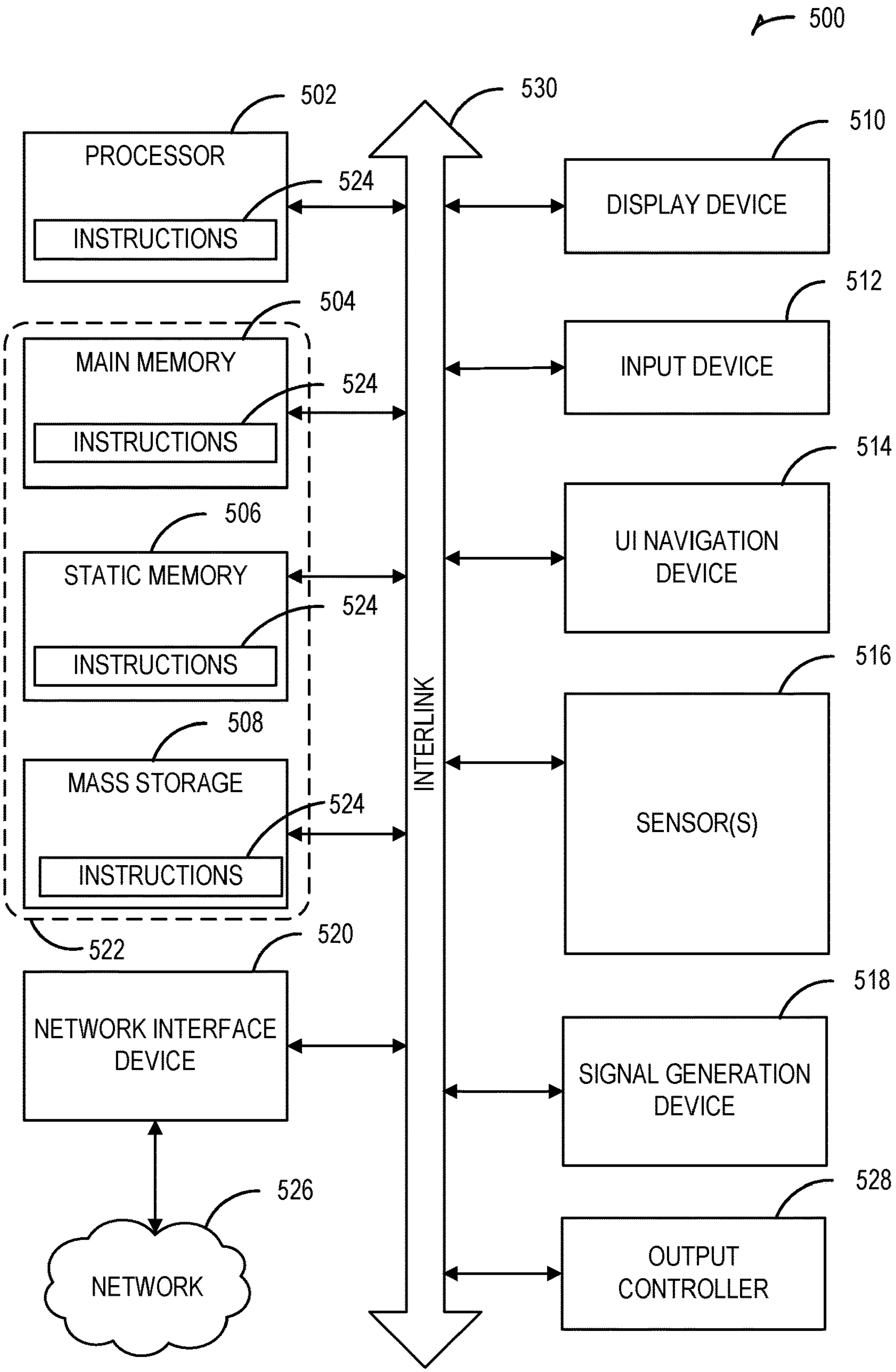
FIG. 5 is a block diagram of an example of an apparatus, device, or machine upon which any one or more of the techniques (e.g., methodologies) discussed herein may perform.

FIG. 5 is a block diagram of an example of an apparatus, device, or machine 500 upon which any one or more of the techniques (e.g., methodologies) discussed herein may perform. In alternative embodiments, the machine 500 may operate as a standalone device or may be connected (e.g., networked) to other machines. In a networked deployment, the machine 500) may operate in the capacity of a server machine, a client machine, or both in server-client network environments. In an example, the machine 500 may act or operate as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out or conduct a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out or conduct portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, field programmable gate array (FPGA), or any combination thereof), a main memory 504 and a static memory 506, some or all of which may communicate with each other via an interlink (e.g., bus) 530. The machine 500 may further include a display unit 510, an input device 512 (e.g., a keyboard or other alphanumeric input device), and a user interface (UI) navigation device 514 (e.g., a mouse). In an example, the display unit 510, input device 512 and UI navigation device 514 may be a touch screen display. The machine 500 may additionally include a storage device 508 (e.g., drive unit or other similar mass storage device or unit), a signal generation device 518 (e.g., a speaker), a network interface device 520 connected to a network 526, and one or more sensors 516, such as a global positioning system (GPS) sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 508 may include a machine readable medium 522 on which is stored one or more sets of data structures or instructions 524 (e.g., software) embodying or used by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 508 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524. The term "machine readable medium" may include any medium that is capable of storing, encoding, or carrying instructions for execution by the machine 500 and that cause the machine 500 to perform any one or more of the techniques of the present disclosure, or that is capable of storing, encoding, or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

ADDITIONAL NOTES & EXAMPLES

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a." "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising." "including." and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general-purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Example 1 is a method of radiation therapy data visualization, the method comprising: determining a data set corresponding to visualization data to be displayed in an application user interface, the data set including one or more Digital Imaging and Communications in Medicine (DICOM) objects; receiving a request for the data set at an application programming interface (API), wherein the API is configured to access multiple sources of DICOM objects; processing the requested data set, wherein processing the requested data set includes, optimizing the requested data set; verifying the request for the data set, and providing, responsive to the verifying, a client device with access to the processed data set to enable visualization of the processed data in the application user interface.

In Example 2, the subject matter of Example 1 includes, wherein optimizing the requested data set includes optimizing the requested data set for visualization without visualizing the requested data set.

In Example 3, the subject matter of Examples 1-2 includes, wherein an environment comprising the multiple sources of DICOM objects includes a multi-application and a multi-tenant environment, and wherein the API retrieves the requested data set from a cached data source.

In Example 4, the subject matter of Examples 1-3 includes, wherein processing the requested data set includes: removing identifying information of a patient, wherein removing identifying information of the patient includes extracting a portion of pixel data from the one or more DICOM objects.

In Example 5, the subject matter of Examples 1~4 includes, creating a secure key corresponding to the one or more DICOM objects; and verifying, in response to receiving the API request, that the secure key corresponds to the requested data set.

In Example 6, the subject matter of Example 5 includes, caching the processed data set; receiving a second request for the data set at the API, the request including a second secure key; verifying, in response to receiving the second request, that the second secure key corresponds to the requested data set; and responsive to the verifying, providing a second client device access to the cached processed data set for visualization.

In Example 7, the subject matter of Examples 5-6 includes, wherein the request for the data set at the API includes the secure key, wherein the secure key is unique to the API request and only allows access to a specific combination of the one or more DICOM objects in the data set, and wherein the secure key is provided in a JSON web token (JWT).

In Example 8, the subject matter of Example 7 includes, wherein to verify that the secure key corresponds to the requested data set the API validates the JWT using a public key, and wherein the public key is configured to: validate that the client device is a valid source to request the data set; and validate that the request for the data set has not been modified or corrupted in transit from the client device.

In Example 9, the subject matter of Examples 5-8 includes, wherein the secure key includes a message digest, the message digest including a hash generated from a list of each of the one or more DICOM objects, and wherein the hash is generated from one or more of: a list of images, one or more spatial registration objects, a structure set, a radiotherapy plan, or a radiotherapy dose to be visualized.

In Example 10, the subject matter of Examples 5-9 includes, transmitting secure key to a renderer of the client device.

In Example 11, the subject matter of Examples 5-10 includes, wherein determining the data set and creating the secure key is performed by a first server, wherein the first server generates the secure key using a private key, and wherein receiving the request for the data set, verifying that the secure key corresponds to the requested data set, processing the requested data set, and providing the client device access to the processed data set is performed by a second server different than the first server.

Example 12 is a system for radiation therapy data visualization, the system comprising: processing circuitry; and memory, including instructions stored thereon, which, when executed by the processing circuitry, cause the processing circuitry to: determine a data set corresponding to visualization data to be displayed in an application user interface, the data set including one or more Digital Imaging and Communications in Medicine (DICOM) objects; create a secure key corresponding to the one or more DICOM objects; receive a request for the data set at an application programming interface (API), the request including the secure key, wherein the API is configured access multiple sources of DICOM objects; verify, in response to receiving the API request, that the secure key corresponds to the requested data set; process the requested data set to remove identifying information, wherein the processing includes: optimizing the requested data set for visualization without visualizing the requested data set; and caching the optimized data set; and responsive to the verifying, provide a client device with access to the processed data set to enable visualization of the data in the application user interface.

In Example 13, the subject matter of Example 12 includes, wherein an environment comprising the multiple sources of DICOM objects includes at least one of a multi-application or a multi-tenant environment, and wherein the API retrieves the requested data set from a cached data source.

In Example 14, the subject matter of Examples 12-13 includes, wherein the secure key is provided in a JSON web token (JWT), and wherein to verify that the secure key corresponds to the requested data set the API validates the JWT using a public key.

In Example 15, the subject matter of Example 14 includes, wherein the public key is configured to: validate that the client device is a valid source to request the data set; and validate that the request for the data set has not been modified or corrupted in transit from the client device.

In Example 16, the subject matter of Examples 12-15 includes, wherein the secure key only allows access to a specific combination of the one or more DICOM objects in the data set, wherein the secure key includes a message digest, the message digest including a hash generated from a list of each of the one or more DICOM objects, and wherein the hash is generated from one or more of: a list of images, one or more spatial registration objects, a structure set, a radiotherapy plan, or a radiotherapy dose to be visualized.

In Example 17, the subject matter of Examples 12-16 includes, wherein processing the requested data set includes: extracting a portion of pixel data from the one or more DICOM objects.

Example 18 is a non-transitory computer-readable medium with instructions stored thereon that, when executed by a processor of a computing device, cause the processor to: determining a data set corresponding to visualization data to be displayed in an application user interface, the data set including one or more Digital Imaging and Communications in Medicine (DICOM) objects; create a secure key corresponding to the one or more DICOM objects; receive a request for the data set at an application programming interface (API), the request including the secure key, wherein the API is configured to access multiple sources of DICOM objects; verify, in response to receiving the API request, that the secure key corresponds to the requested data set; process the requested data set to remove identifying information, wherein processing the requested data set includes, optimizing the requested data set; and responsive to the verifying, provide a client device with access to the processed data set to enable visualization of the data in the application user interface.

In Example 19, the subject matter of Example 18 includes, wherein optimizing the requested data set includes optimizing the requested data set for visualization without visualizing the requested data set, and wherein the instructions further cause the processor to: cache the optimized data set.

In Example 20, the subject matter of Examples 18-19 includes, wherein processing the requested data set includes: extracting a portion of pixel data from the one or more DICOM objects.

In Example 21, the subject matter of Examples 18-20 includes, wherein the secure key is provided in a JSON web token (JWT), wherein to verify that the secure key corresponds to the requested data set the API validates the JWT using a public key, and wherein the public key is configured to: validate that the client device is a valid source to request the data set; and validate that the request for the data set has not been modified or corrupted in transit from the client device.

Example 22 is a method of caching radiation therapy data visualization, the method comprising: receiving a request for a data set corresponding to a patient from a first client, the data set including one or more Digital Imaging and Communications in Medicine (DICOM) objects; retrieving the data set from a data source; processing the data set; caching the processed data set; providing the first client with access to the processed data to enable visualization of the processed data; receiving a request for the data set corresponding to the patient from a second client; and retrieving the cached processed data set.

In Example 23, the subject matter of Example 22 includes, wherein the request from the first client is from a server associated with a first client device.

In Example 24, the subject matter of Examples 22-23 includes, wherein the request for the data set includes a unique secure key provided in a first JSON web token (JWT), and wherein the first JWT is verified using a public key configured to: validate that the first client is a valid source to request the data set; and validate that the request for the data set has not been modified or corrupted in transit from the first client.

In Example 25, the subject matter of Examples 22-24 includes, providing the second client with access to the processed data from the cache to enable visualization of the processed data.

In Example 26, the subject matter of Example 25 includes, wherein the request from the second client is from a server associated with a second client device.

In Example 27, the subject matter of Example 26 includes, wherein the request for the data set from the second client includes a unique secure key provided in a JSON web token (JWT), and wherein the JWT is verified using a public key configured to: validate that the second client device is a valid source to request the data set; and validate that the request for the data set has not been modified or corrupted in transit from the second client device.

In Example 28, the subject matter of Examples 22-27 includes, wherein processing the requested data set includes: optimizing the data set for visualization without visualizing the data set; and extracting a portion of pixel data from the one or more DICOM objects.

Example 29 is a system for caching radiation therapy data visualization, the system comprising: processing circuitry; and memory including instructions that, when executed by the processing circuitry, cause the processing circuitry to: receive a request for a data set corresponding to a patient from a first client, the data set including one or more Digital Imaging and Communications in Medicine (DICOM) objects; retrieve the data set from a data source; process the data set, wherein processing the data set includes: remove identifying information of the patient from the one or more DICOM objects; and optimize the data set for visualization without visualizing the data set; cache the processed data set; and provide the first client with access to the processed data to enable visualization of the processed data.

In Example 30, the subject matter of Example 29 includes, wherein the request from the first client is from a server associated with a first client device.

In Example 31, the subject matter of Example 30 includes, wherein the request for the data set includes a unique secure key provided in a first JSON web token (JWT), and wherein the first JWT is verified using a public key configured to: validate that the first client device is a valid source to request the data set; and validate that the request for the data set has not been modified or corrupted in transit from the first client device.

In Example 32, the subject matter of Examples 29-31 includes, the processing circuitry further to: receive a request for the data set corresponding to the patient from a second client; retrieve the cached processed data set; and provide the second client with access to the processed data from the cache to enable visualization of the processed data.

In Example 33, the subject matter of Example 32 includes, wherein the request from the second client is from a server associated with a second client device.

In Example 34, the subject matter of Example 33 includes, wherein the request for the data set from the second client includes a unique secure key provided in a JSON web token (JWT), and wherein the JWT is verified using a public key configured to: validate that the second client device is a valid source to request the data set; and validate that the request for the data set has not been modified or corrupted in transit from the second client device.

In Example 35, the subject matter of Examples 29-34 includes, wherein processing the requested data set includes: extracting a portion of pixel data from the one or more DICOM objects.

Example 36 is a non-transitory computer-readable medium with instructions stored thereon that, when executed by a processor of a computing device, cause the processor to: receive a request for a data set corresponding to a patient from a first client, the data set including one or more Digital Imaging and Communications in Medicine (DICOM) objects; retrieve the data set from a data source; process the data set, wherein processing the data set includes: remove identifying information of the patient from the one or more DICOM objects; and optimize the data set for visualization without visualizing the data set; cache the processed data set; and provide the first client with access to the processed data to enable visualization of the processed data.

In Example 37, the subject matter of Example 36 includes, wherein the request from the first client is from a server associated with a first client device.

In Example 38, the subject matter of Example 37 includes, wherein the request for the data set includes a unique secure key provided in a first JSON web token (JWT), and wherein the first JWT is verified using a public key configured to: validate that the first client device is a valid source to request the data set; and validate that the request for the data set has not been modified or corrupted in transit from the first client device.

In Example 39, the subject matter of Examples 36-38 includes, wherein the instructions further cause the processor to: receive a request for the data set corresponding to the patient from a second client; retrieve the cached processed data set; and provide the second client with access to the processed data from the cache to enable visualization of the processed data.

In Example 40, the subject matter of Example 39 includes, wherein the request from the second client is from a server associated with a second client device.

In Example 41, the subject matter of Example 40 includes, wherein the request for the data set from the second client includes a unique secure key provided in a JSON web token (JWT), and wherein the JWT is verified using a public key configured to: validate that the second client device is a valid source to request the data set; and validate that the request for the data set has not been modified or corrupted in transit from the second client device.

In Example 42, the subject matter of Examples 36-41 includes, wherein processing the requested data set includes: extracting a portion of pixel data from the one or more DICOM objects.

Example 43 is at least one machine-readable medium including instructions that, when executed by processing circuitry, cause the processing circuitry to perform operations to implement of any of Examples 1-42.

Example 44 is an apparatus comprising means to implement of any of Examples 1-42.

Example 45 is a system to implement of any of Examples 1-42.

Example 46 is a method to implement of any of Examples 1-42.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method of radiation therapy data visualization, the method comprising:

determining a data set corresponding to visualization data to be displayed in an application user interface, the data set including one or more Digital Imaging and Communications in Medicine (DICOM) objects;

receiving a request for the data set at an application programming interface (API), wherein the API is configured to access multiple sources of DICOM objects;

processing the requested data set, wherein processing the requested data set includes optimizing the requested data set;

verifying the request for the data set;

providing, responsive to the verifying, a client device with access to the processed data set to enable visualization of the processed data in the application user interface;

caching the processed data set;

receiving a second request for the data set at the API; and providing a second client device with access to the cached processed data set to enable visualization without reprocessing the data set.

2. The method of claim 1, wherein optimizing the requested data set includes optimizing the requested data set for visualization without visualizing the requested data set.

3. The method of claim 1, wherein an environment comprising the multiple sources of DICOM objects includes a multi-application and a multi-tenant environment, and wherein the API retrieves the requested data set from a cached data source.

4. The method of claim 1, wherein processing the requested data set includes:

removing identifying information of a patient, wherein removing identifying information of the patient includes extracting a portion of pixel data from the one or more DICOM objects.

5. The method of claim 1, further comprising:

creating a secure key corresponding to the one or more DICOM objects; and verifying, in response to receiving the API request, that the secure key corresponds to the requested data set.

6. The method of claim 5, wherein the second request includes a second secure key, and wherein the method further comprises:

verifying, in response to receiving the second request, that the second secure key corresponds to the requested data set; and responsive to the verifying, providing the second client device with access to the cached processed data.

7. The method of claim 5, wherein the request for the data set at the API includes the secure key, wherein the secure key is unique to the API request and only allows access to a specific combination of the one or more DICOM objects in the data set, and wherein the secure key is provided in a JSON web token (JWT).

8. The method of claim 7, wherein to verify that the secure key corresponds to the requested data set, the API validates the JWT using a public key, and wherein the public key is configured to:

validate that the client device is a valid source to request the data set; and validate that the request for the data set has not been modified or corrupted in transit from the client device.

9. The method of claim 5, wherein the secure key includes a message digest, the message digest including a hash generated from a list of each of the one or more DICOM objects, and wherein the hash is generated from one or more of: a list of images, one or more spatial registration objects, a structure set, a radiotherapy plan, or a radiotherapy dose to be visualized.

10. The method of claim 5, further comprising:

transmitting secure key to a renderer of the client device.

11. The method of claim 5, wherein determining the data set and creating the secure key is performed by a first server, wherein the first server generates the secure key using a private key, and wherein receiving the request for the data set, verifying that the secure key corresponds to the requested data set, processing the requested data set, and providing the client device access to the processed data set is performed by a second server different than the first server.

12. A system for radiation therapy data visualization, the system comprising:

processing circuitry; and memory, including instructions stored thereon, which, when executed by the processing circuitry, cause the processing circuitry to:

determine a data set corresponding to visualization data to be displayed in an application user interface, the data set including one or more Digital Imaging and Communications in Medicine (DICOM) objects;

create a secure key corresponding to the one or more DICOM objects;

receive a request for the data set at an application programming interface (API), the request including the secure key, wherein the API is configured to access multiple sources of DICOM objects;

verify, in response to receiving the API request, that the secure key corresponds to the requested data set;

process the requested data set to remove identifying information, wherein the processing includes:

optimizing the requested data set for visualization without visualizing the requested data set; and caching the optimized data set;

responsive to the verifying, provide a client device with access to the processed data set to enable visualization of the processed data at the application user interface;

receive a second request for the data set at the API, the second request including a second secure key;

verify, in response to receiving the second request, that the second secure key corresponds to the requested data set; and responsive to verifying the second secure key, provide a second client device with access to the cached optimized data set to enable visualization without reprocessing the data set.

13. The system of claim 12, wherein an environment comprising the multiple sources of DICOM objects includes at least one of a multi-application or a multi-tenant environment, and wherein the API retrieves the requested data set from a cached data source.

14. The system of claim 12, wherein the secure key is provided in a JSON web token (JWT), and wherein to verify that the secure key corresponds to the requested data set the API validates the JWT using a public key.

15. The system of claim 14, wherein the public key is configured to:

validate that the client device is a valid source to request the data set; and validate that the request for the data set has not been modified or corrupted in transit from the client device.

16. The system of claim 12, wherein the secure key only allows access to a specific combination of the one or more DICOM objects in the data set, wherein the secure key includes a message digest, the message digest including a hash generated from a list of each of the one or more DICOM objects, and wherein the hash is generated from one or more of: a list of images, one or more spatial registration objects, a structure set, a radiotherapy plan, or a radiotherapy dose to be visualized.

17. The system of claim 12, wherein processing the requested data set includes:

extracting a portion of pixel data from the one or more DICOM objects.

18. A non-transitory computer-readable medium with instructions stored thereon that, when executed by a processor of a computing device, cause the processor to:

determine a data set corresponding to visualization data to be displayed in an application user interface, the data set including one or more Digital Imaging and Communications in Medicine (DICOM) objects;

create a secure key corresponding to the one or more DICOM objects;

receive a request for the data set at an application programming interface (API), the request including the secure key, wherein the API is configured to access multiple sources of DICOM objects;

verify, in response to receiving the API request, that the secure key corresponds to the requested data set;

process the requested data set to remove identifying information, wherein processing the requested data set includes optimizing the requested data set;

cache the processed data set:

responsive to the verifying, provide a client device with access to the processed data set to enable visualization of the data in the application user interface;

receive a second request for the data set at the API, the second request including a second secure key;

verify, responsive to receiving the second request, that the second secure key corresponds to the requested data set; and responsive to verifying the second secure key, provide a second client device with access to the cached processed data set to enable visualization without reprocessing the data set.

19. The non-transitory computer-readable medium of claim 18, wherein optimizing the requested data set includes optimizing the requested data set for visualization without visualizing the requested data set, and wherein the instructions further cause the processor to:

cache the optimized data set.

20. The non-transitory computer-readable medium of claim 18, wherein processing the requested data set includes:

extracting a portion of pixel data from the one or more DICOM objects.

21. The non-transitory computer-readable medium of claim 18, wherein the secure key is provided in a JSON web token (JWT), wherein to verify that the secure key corresponds to the requested data set the API validates the JWT using a public key, and wherein the public key is configured to:

validate that the client device is a valid source to request the data set; and validate that the request for the data set has not been modified or corrupted in transit from the client device.

* * * * *